United States Patent [19]

McLean et al.

[11] Patent Number: 4,941,480
[45] Date of Patent: Jul. 17, 1990

[54] DEVICE FOR IMMOBILIZING LIMB OF PATIENT

[76] Inventors: Philip W. McLean, 3356 Revere Rd.; Russell R. English, 3834 Broadview Rd., both of Richfield, Ohio 44286.

[21] Appl. No.: 362,481

[22] Filed: Jun. 7, 1989

[51] Int. Cl.⁵ ............................................ A61F 13/00
[52] U.S. Cl. ...................................... 128/878; 128/879
[58] Field of Search ............... 128/77, 87 R, 80 R, 128/877, 878, 879, DIG. 6, DIG. 15

[56] References Cited

U.S. PATENT DOCUMENTS

| | | | |
|---|---|---|---|
| 3,196,870 | 7/1965 | Sprecher et al. | 128/DIG. 6 |
| 3,232,289 | 2/1966 | Zimmerman | 128/87 R |
| 3,423,095 | 1/1969 | Cox | 128/878 |
| 3,439,673 | 4/1969 | Sprecher | 128/877 |
| 3,568,671 | 3/1971 | Graham | 128/87 R |
| 3,719,187 | 3/1973 | Ulansey | 128/87 R |
| 3,776,225 | 12/1973 | Lonardo | 128/877 |
| 3,800,789 | 4/1974 | Schloss | 128/90 |
| 3,815,587 | 6/1974 | Guerrant | 128/77 |
| 3,827,107 | 8/1974 | Moore | 24/16 R |
| 3,896,799 | 7/1975 | Seeley | 128/DIG. 6 |
| 3,901,225 | 8/1975 | Sconce | 128/89 R |
| 3,903,878 | 9/1975 | Spann | 128/77 |
| 4,019,504 | 4/1977 | Sterling | 128/88 |
| 4,081,150 | 3/1978 | Tyson | 128/402 |
| 4,156,425 | 5/1979 | Arkans | 128/24 R |
| 4,202,325 | 5/1980 | Villari et al. | 128/24 R |
| 4,215,687 | 8/1980 | Shaw | 128/169 |
| 4,265,232 | 5/1981 | Stonich | 128/877 |
| 4,286,588 | 9/1981 | Lovegrove | 128/DIG. 6 |
| 4,503,849 | 3/1985 | Morgan et al. | 128/877 |
| 4,587,962 | 5/1986 | Greene et al. | 128/80 H |
| 4,624,244 | 11/1986 | Taheri | 128/24 R |
| 4,625,719 | 12/1986 | Chambers | 128/94 |
| 4,693,239 | 9/1987 | Clover, Jr. | 128/80 F |
| 4,730,801 | 3/1988 | Cloward | 128/77 |

*Primary Examiner*—Robert A. Hafer
*Assistant Examiner*—Charles H. Sam
*Attorney, Agent, or Firm*—Oldham & Oldham Co.

[57] ABSTRACT

Device for immobilizing a patient's limb. The device comprises an elongated, three-sided, resilient support member of generally U-shaped cross-section, open at the top and comprising a base or bottom wall and a pair of side walls extending upwardly from the base, and fastener means extending from one side wall to the other across the open top of the support member. The support member is preferably made of a closed cell plastic foam material, coated with a thin adherent washable coating. The side walls are preferably perpendicular to the base, defining an opening of rectangular cross-section for receiving a patient's limb or portion thereof. Fastener means may include either a plurality of transversely extending straps (preferably Velcro) or a plastic sheet having means (such as short Velcro strips) which will engage the side walls.

6 Claims, 2 Drawing Sheets

DEVICE FOR IMMOBILIZING LIMB OF PATIENT

TECHNICAL FIELD

This invention relates to devices for immobilizing and supporting a limb of a patient. More particularly, this invention relates to a device for immobilizing both effectively and comfortably an arm of a patient who requires intraveneous (I.V.) administration of fluid.

BACKGROUND ART

Intraveneous administration of fluids to a patient is required in a number of medical situations ranging from emergency treatment to long term care. For example, it is sometimes necessary to administer fluid intravenously in emergency treatment while a patient is being transported via ambulance. Many patients in hospitals and nursing homes also require I.V. administration of fluid.

Various devices for supporting or immobilizing an arm of a patient for I.V. administration of fluids are known. Among these are the devices shown in U.S. Pat. No. 3,196,870 to Sprecher et al, U.S. Pat. No. 3,439,673 to Sprecher, and U.S. Pat. No. 3,776,225 to Lonardo. The device of U.S. Pat. No. 3,196,870 comprises a pair of elongated steel bars linked by a plurality of cross straps. A generally similar apparatus is shown in U.S. Pat. No. 3,439,673. The rigid bars in both devices are disposed alongside the patient's arm. U.S. Pat. No. 3,776,225 discloses a forearm splint which includes a longitudinally extending rigid plastic splint member (illustrated as formed in two sections which are joined together) which includes shaped hand-supporting and elbow-supporting portions.

A number of other devices for supporting and/or immobilizing a patient's limb (commonly called orthosis devices), are also known. For example, U.S. Pat. No. 3,903,878 to Spann shows a device for supporting a patient's forearm with particular reference to support of an arm or leg during physical therapy. The device shown therein is a resilient polyurethane foam block, cut to provide a longitudinally extending polygonal support member having a longitudinally extending internal groove of circular cross-section for receiving a limb of a patient. This groove is open to the exterior via a slot whose width is slightly less than the diameter of the groove. Transversely extending velcro straps are provided for fastening the device to the arm or leg of a patient.

Other orthosis devices include the temporary splint shown in U.S. Pat. No. 3,800,789 to Schloss, which is particularly suitable for use on the lower leg and foot, and the adjustable arm sling shown in U.S. Pat. No. 4,625,719 to Chambers.

While a number of devices for supporting and/or immobilizing a patient's limb for various medical purposes are known, including some which are specifically disclosed as being useful for patients receiving I.V. fluids, none has achieved the combination of effective immobilization, patient comfort and reasonable cost necessary for widespread acceptance. In fact, many hospitals at present do not use any of the available devices, but simply tie the patient's arm to the bed with adhesive tape or simply place a pillow under the patient's elbow without immobilizing the arm, when administering intravenous fluid to a patient. There is a need for an orthosis which combines effective immobilization, patient comfort and reasonable cost and also take risk off of medical personnel, that the I.V. will remain in place and not be tampered with.

DISCLOSURE OF THE INVENTION

The present invention provides a device for immobilizing a limb of a patient, comprising a resilient elongated, 3-sided support member of generally U-shaped cross-section which support member comprises a base and a pair of sides extending upwardly from the base, and which is open at the top; and fastener means adapted to be removably attached to the upwardly extending sides to extend across the open top of the support member.

BRIEF DESCRIPTION OF THE DRAWINGS

In the drawings:

FIG. 6 is a perspective view of a limb immobilizing device according to a second embodiment of this invention. The fastener means according to this second embodiment differs from that shown in the first embodiment, but the limb support member is the same in both embodiments.

FIG. 7 is a plan view of the fastener means according to the second embodiment of the invention.

FIG. 8 is a side, edge view of the fastener means of the second embodiment.

BEST MODE FOR CARRYING OUT THE INVENTION

Figure 1:
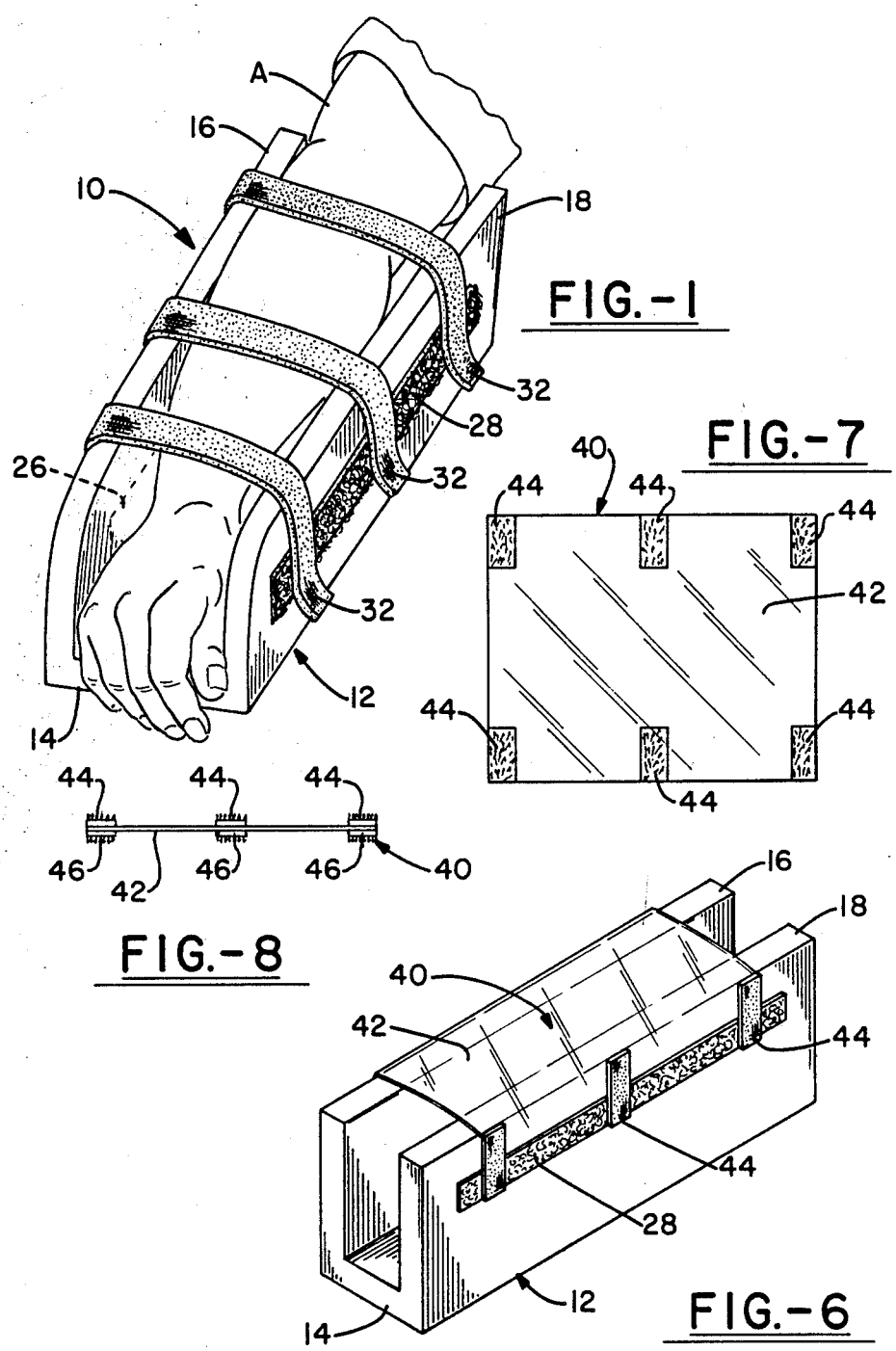
FIG. 1 is a perspective view of a limb immobilizing device according to a first embodiment of the invention, showing a patient's arm immobilized therein.
Figure 2:
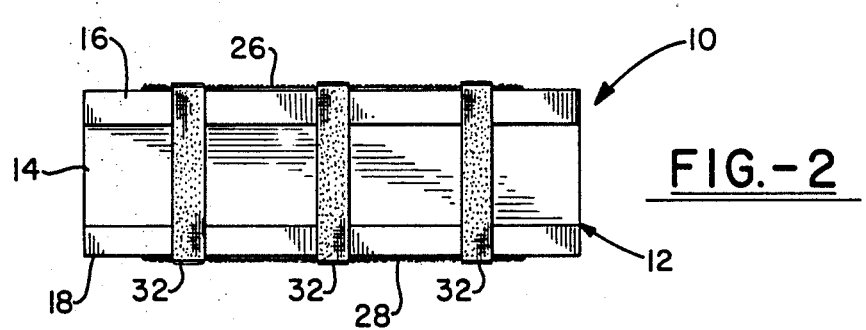
FIG. 2 is a top plan view of the limb immobilizing device shown in FIG. 1.
Figure 3:
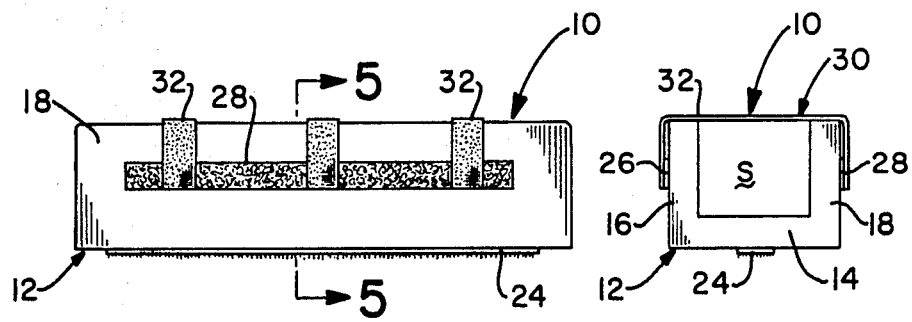
FIG. 3 is a side elevational view of the limb immobilizing device shown in FIG. 1.
Figure 4:
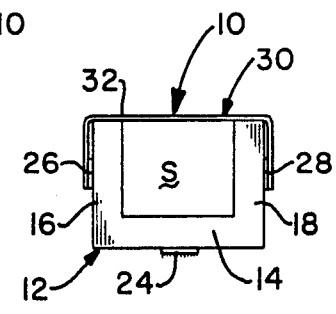
FIG. 4 is an end elevational view of the limb immobilizing device shown in FIG. 1.

A limb immobilizing device according to the first embodiment of this invention will now be described with particular reference to FIGS. 1-5.

Referring to FIGS. 1-5, 10 represents a limb immobilizing device generally according to this invention. Limb immobilizing device 10 comprises a resilient, elongated, 3-sided support member 12 of generally U-shape cross-section. Support member 12 comprises a base, or bottom wall 14, and a pair of side walls 16,18 which are at right angles to the base and which extend upwardly from the opposite side edges of base 14. Base 14 and side walls 16,18 together define an interior space S (shown in FIGS. 4 and 5) of rectangular cross-section and open at the top, for receiving a limb of a patient.

Both the outside and the inside surfaces of bottom wall 14 and side walls 16,18 are preferably planar. Also, all three walls are preferably of uniform thickness. Therefore, the angles of intersection between bottom wall 14 and side walls 16,18 are equal, whether measured at the intersections of the respective outside surfaces or at the intersections of the respective inside surfaces. In the preferred embodiment shown, all such angles of intersection are right angles. It is also possible to dispose the sides 16,18 at an obtuse angle, say 120° (but seldom much greater than that) as measured on the inside surfaces, with respect to the base 14.

Figure 5:
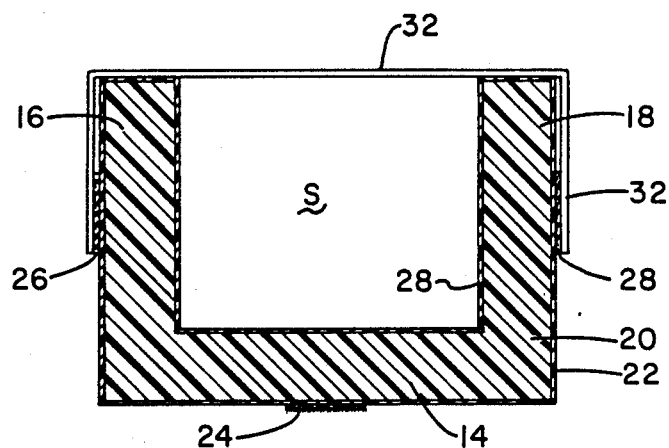
FIG. 5 is a vertical sectional view taken along line 5—5 of FIG. 3.

Referring now to FIG. 5, support member 12 comprises a resilient core 20, preferably a plastic foam material and more particularly a closed cell plastic foam material, coated with a thin adherent water-proof, washable coating 22. A closed cell foam plastic material, in which the cells of the foam do not communicate with each other, is preferred because closed cell foams do not absorb water and because the gas in the close cells does not escape and the material retains its resiliency under load. The core 20 must be resilient, i.e. it must be deformable under load and have memory so that it returns to its original or normal position when the load or stress is removed. Suitable plastic foam materials, including polyurethane (e.g., high resilience or HR foam) or polyvinyl may be used. The latter is available in sheet form in large rolls from Uniroyal, Inc.

Coating 22 must be waterproof and washable, must adhere well to the core or substrate 20, must not crack or flake off when the core 20 is bent or flexed, and desirably is waterproof, washable and impervious to water. Resistance to attack by common organic liquids, such as alcohol, ether, storing detergents and sterilizing compositions is also desirable. A particularly suitable coating is a solvent based vinyl coating, comprising a vinyl resin, pigment and a solvent. Suitable coatings of this type are designated as Flexabar Marine or Athletic Vinyl, which are available from Flexabar, Northvale, N.J. Such coatings may be applied by conventional techniques, such as spraying or dipping. The Flexabar coatings are preferably applied by dipping after first adjusting the product with thinner (e.g. 1/1 toluene/-methyl ethyl ketone) to a viscosity of 12-15 sec. at room temperature, using a No. 3 Zahn Cup. The coating may be applied to any desired thickness; for the purposes of this invention, a coating about 0.020" over the entire exposed surface of core 20 is highly desirable.

Support member 12 may be formed by joining together three (3) pieces of closed cell plastic foam all in the shape of rectangular solids in which the thickness is typically substantially less than either the length or the width, so that the longitudinally extending side edges of the piece forming base 14 is flush against the inside surfaces of the pieces forming side walls 16 and 18. Conventional plastic joining techniques may be used. Coating 22 is applied after the pieces have been so joined. It will be appreciated that this mode of assembly is much less costly than formation of support member 12 by cutting from a rectangular plastic foam block would be. The mode of assembly described is made possible by the fact that bottom wall 14 and side walls 16,18 are all of uniform thickness, typically about 1" and in no case more than about 1¼".

Support member 12 may be of any desired dimensions, depending on the desired service. For supporting the entire forearm of a patient from (and including) the elbow to the hand, the overall length may be 17", the overall width may be 6" and the overall height may be 4", and the thickness of each wall member 14, 16 and 18 may be from about 1.0 to about 1.125". Based on a wall thickness of 1.0", the interior space S is of rectangular cross-section and is 4.0" wide and 3.0" high. A shorter version, particularly suitable for immobilizing the forearm of a patient while leaving the elbow and wrist free, may be about 9 to 9.5" long and may have the same width, height and wall thickness as the first mentioned specific embodiment. Each of these specific embodiments may be formed of three pieces of plastic foam having the same size, i.e., 17 in. × 4 in. × 1 in. or 9-9.5 in. × 4 in. × 1 in., as the case may be. It will be appreciated that these dimensions are representative and that other dimensions are permissible within the scope of the invention. The dimensions indicated are suitable for about 97 percent of the adult population. Even if the patient's arm is appreciably smaller than the 4" interior space width provided in the preferred embodiment, the resilient nature of support member 12 permits the upper edges of side walls 16,18 to be pulled more closely together by the fastener means to be hereinafter described, so that the support member provides adequate support.

A longitudinally extending Velcro strip 24 may be provided on the bottom surface of bottom wall 14, for securing the immobilizing device 10 to another structure, such as the side rail of a gurney of an ambulance, a hospital bed, etc. The outside surfaces of side walls 16,18 may also be provided with longitudinally extending Velcro strips 26,28 respectively; these Velcro strips form part of the fastener means which permits side walls 16,18 to be flexed inwardly and which also provides a secure arrangement in which an I.V. tube inserted into the patient's elbow or forearm will stay in place while patient comfort is provided.

The fastener means, according to a first embodiment of this invention, further includes a plurality of transversely extending Velcro strips 32 (3 are shown), which engage the longitudinally extending strips 22,24 and which extend cross the open top of device 10. The fastener elements on straps 32 and on strips 22,24 are complimentary. One set of Velcro fastener elements (e.g. straps 32) have hooks which engage the pile of the other set of fastener elements (e.g., strips 22 and 24). Straps 32, plus the resilient nature of device 10, make it possible to adjust the width of the opening between the respective top edges of side walls 16,18.

A second embodiment of fastener means 40 is shown in FIGS. 6–8. As best seen in FIG. 7, this embodiment comprises a thin transparent plastic sheet (e.g. polyvinylchloride) with two (2) sets 44,46 of short, transversely extending Velcro strips (preferably with 6 strips in each set as shown) on opposite sides of sheet 42. Each strip extends transversely inward from a side edge of rectangular plastic sheet 42. Each strip 44 in the first set is placed back-to-back with a strip 46 in the second set. Fasteners on these strips 44 and 46 are complimentary with the fastener elements on longitudinal strips 26,28. That is, strips 44,46 may have hooks which engage pile fastener elements on strips 26,28, or vice versa. Fastener sheet 42 is reversible, i.e. either side may face outwardly, due to the fact that Velcro strips 44 and 46 are provided on both sides. Fastener means 40 also affords some adjustability in the sides of the opening or gap between the respective top edges of side walls 16 and 18.

The fastener means 40 of the second embodiment is particularly advantageous for use on a patient who is receiving fluid via I.V. administration. The plastic sheet serves a a tamper proof shield which helps to protect the I.V. tubes from accidental removal.

A shorter version of the device 10 of this invention may be provided when it is desired to immobilize only the wrist and not the entire forearm of the patient. This shorter version is like the forearm immobilizing device shown in every respect except length. Normally only two straps 32 are required with the shorter version.

Device 10 of this invention can also be made in a larger size for accommodating a leg of a patient. While the device 10 of this invention is particularly useful for a patient who is receiving fluid via I.V. administration (which is usually introduced into the patient at the elbow or along the forearm), this device is also useful in other situations where immobilization of a patient's limb or portion thereof is required for medical reasons.

A device of this invention may be used in emergency medical care to immobilize a limb of a patient who is being transported by ambulance. This device is useful whether or not the patient is receiving I.V. fluid, but is particularly useful when I.V. fluid is required. A device of this invention is also useful to support and immobilize a limb of a patient in other situations, as for example, a hospital or nursing home patient in bed who is receiving I.V. fluid. The device 10 is also useful for a patient in a wheelchair, either for the purpose of permitting I.V. fluid administration or simply to provide support for the patient's forearm in the most comfortable manner possible.

The device of this invention is intended primarily for use by trained medical personnel, such as a physician, nurse, paramedic or I.V. therapist especially the latter two. The user, i.e. the trained medical person, places the patient's limb (usually the forearm) inside the opening S, pulls the straps 32 or sheet 42 so that the sides 16,18 fit snuggly around the patient's limb. The bottom wall 14 rests on a suitable support surface, e.g. the side rail of a gurney of an ambulance, a hospital bed sheet, etc., which preferably has a Velcro fastener complimentary to fastener strip 24. The gap between the top edges of side walls 16,18 is adjustable as previously noted.

Storage of the device is facilitated because of its light weight, about 8 to 10 ounces. The device is easily seocured to an ambulance wall or ceiling by means of Velcro straps. Storage and dismantle also makes it very accessible because it is not stored in a cabinet. The design of this device also provides a place (i.e., S) for storage of an I.V bag of solution and an administration kit, which typically contains a tourniquet, adhesive tape, and other materials needed for on-board administration to a sick or injured patient who is being transported via ambulance. The hospital can also use this space for storage of materials needed to start I.V. administration. In fact, all the materials needed can be pre-packaged as a kit which is packaged as a kit which is stored inside S. Again, such kit is readily secured to the device of this invention by means of Velcro straps.

While this invention has been described with reference to preferred embodiments thereof, as shown in the accompanying drawings, it should be understod that these embodiments are by way of illustration and not by way of limitation.

What is claimed is:

1. A device for immobilizing a limb of a patient, said device being resilient and comprising:
    (a) a longitudinally extending resilient elongated three-sided support member comprising a resilient core and a thin adherent waterproof, washable coating thereon, said support member being of generally U-shaped cross section, and straight in the longitudinal direction, said support member comprising a bottom wall and a pair of side walls extending upwardly from opposite side edges of said bottom wall, said bottom wall and said side walls each being essentially rectangular in shape and of substantially uniform thickness and having planar outside surfaces and planar inside surfaces, said support member being open at the top; and
    (b) fastener means including a member adapted to be removably attached to said upwardly extending sides and to extend across the open top of said support member.

2. A device according to claim 1 in which said fastener means comprise a plurality of transversly extending Velcro straps extending from one of said side walls to the other across the open top of the support member.

3. A device according to claim 1 in which said fastener means comprises a thin flexible plastic sheet having Velcro fastener elements thereon.

4. A device according to claim 1 in which the core of said support member is made of a resilient plastic foam material.

5. A device according to claim 4 in which said plastic foam material is a closed cell plastic foam material.

6. A device according to claim 1 in which said side walls intersect said bottom wall at right angles.

* * * * *